(12) United States Patent
Burdeniuc

(10) Patent No.: US 6,559,308 B1
(45) Date of Patent: May 6, 2003

(54) METHOD FOR PREPARING HETEROCYCLIC-CARBOXYLIC ACIDS

(75) Inventor: Juan Jesus Burdeniuc, Macungie, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 124 days.

(21) Appl. No.: 09/925,239

(22) Filed: Aug. 9, 2001

(51) Int. Cl.$^7$ ............................................. C07D 241/42
(52) U.S. Cl. ..................... 544/353; 546/110; 546/170; 548/261; 548/304.4; 548/306.4
(58) Field of Search ......................................... 544/353

(56) References Cited

U.S. PATENT DOCUMENTS

| | | | |
|---|---|---|---|
| 3,772,273 A | 11/1973 | Gilbert | ........................ 260/250 |
| 3,960,963 A | 6/1976 | Gavin | |

FOREIGN PATENT DOCUMENTS

| | | | |
|---|---|---|---|
| DE | 4410418 | | 9/1995 |
| EP | 0257518 | | 3/1988 |
| WO | 00/51608 | * | 9/2000 |

OTHER PUBLICATIONS

R. Granger, S. Deadwyler, et al. "Facilitation of Glutamate Receptors Reverses an Age–Associated Memory Impairment in Rats" Synapse, 22, pp. 332–337, 1996.
G. Lynch, M. Kessler, et al., "Psychological Effects of a Drug that Facilitates Brain AMPA Receptors", International Clinical Psychopharmacology, 11, pp. 13–19, 1996.
W. F. Gum, "Structure vs. Reactivity in Quinoxalinecarboxylic Acids and Esters", J. Org. Chem. 30, 3982, 1965.
H. Huang, A. R. Lee, C. I. Lin, et al. , Yixue Yanjiu, 13, 247–54, 1993.
B. Shilling, Ber., 34, pp 902–907, 1901.
A. Tallec, Chem. Abs., vol. 69, 1968, Abs #86512C, p 8073.
V. Cere, D. Dal Monte, E. Sardi, Tetrahedron, 28, 3271, 1972.
M. Hudlicky, "Oxidations in Organic Chemistry", ACS Monograph 186, 1990.
R. A. Sheldon, J. K. Kochi, "Metal–Catalyzed Oxidation of Organic Compounds", Chapter 5, pp. 121–151, Academic Press, 1981.
2–3–Pyrazinedicarboxylic acid: "Organic Synthesis" Coll. vol. 4, pp. 824–827, J. Wiley & Sons, Inc., NY 1963.
R. A. Sheldon, J. K. Kochi, "Metal Catalyzed Oxidation of Organic Compounds", Chapter 7, pp. 189–214, Academic Press, 1981.
J. C. Cavagnol, F. Y. Wiselogle, J. Am. Chem. Soc., 69, 795, 1947.
Thomas D. Waugh, NBS: N–Bromosuccinimide Its Reactions and Uses; Araphoe Chemicals, Inc. Boulder Co. 1951, p 1–41.
Benzoyl Piperadine: "Organic Synthesis", Coll. vol. 1 pp. 108–110, J. Wiley & Sons, Inc. New York, 1943.
European Search Report, 02017635.0–21–1, dated Oct. 31, 2002.
Prasad, A.D., et al., "Vapor Phase Oxidation of 4–Pyridine Methanol to 4–Pyridine Carboxaldehyde," Synth. Commun., vol. 20, No. 21, pp. 3385–3390 (XP001106942).
Oi, Ryu, et al., "Selective Conversion of M–Hydroxybenzyl Alcohol to M–Hydroxybezaldehyde," Chemistry Letters, pp. 1115–1116 (1988) (XP001106256).

* cited by examiner

*Primary Examiner*—Emily Bernhardt
(74) *Attorney, Agent, or Firm*—Michael Leach

(57) ABSTRACT

The present invention relates to a method for preparing quinoxaline-5- and 6-carboxylic acids. The method comprises contacting an aqueous suspension of a 5- or 6-hydroxymethyl quinoxaline with oxygen in the presence of a transition metal catalyst, to form the respective quinoxaline-5- or 6-carboxylic acid. The method for oxidizing benzylic methyl groups may also be employed to prepare a wide variety of heterocyclic carboxylic acid compounds.

7 Claims, No Drawings

METHOD FOR PREPARING HETEROCYCLIC-CARBOXYLIC ACIDS

BACKGROUND OF THE INVENTION

The present invention relates to a method for preparing heterocyclic carboxylic acid compounds, especially quinoxaline-5- and 6-carboxylic acids.

The disclosures referred to herein to illustrate the background of the invention and to provide additional detail with respect to its practice are incorporated herein by reference and, for convenience, are numerically referenced in the following text and respectively grouped in the appended bibliography.

Quinoxaline-6-carboxylic acid is an important chemical intermediate for the preparation of compounds such as AMPHAKINE CX516 [1-(quinoxalin-6-ylcarbonyl) piperidine], a drug being tested for the treatment of Alzheimer's disease, Attention Deficit Hyperactivity Disorder (ADHD), Mild Cognitive Impairment (MCI), Chronic Schizophrenia and male sexual dysfunction (1). The preparation of AMPHAKINE CX516 involves the conversion of 3,4-diaminobenzoic acid to quinoxaline-6-carboxylic acid with sodium glyoxal bisulfite, followed by amidation of the resulting acid with piperidine, as set out below (2, 12).

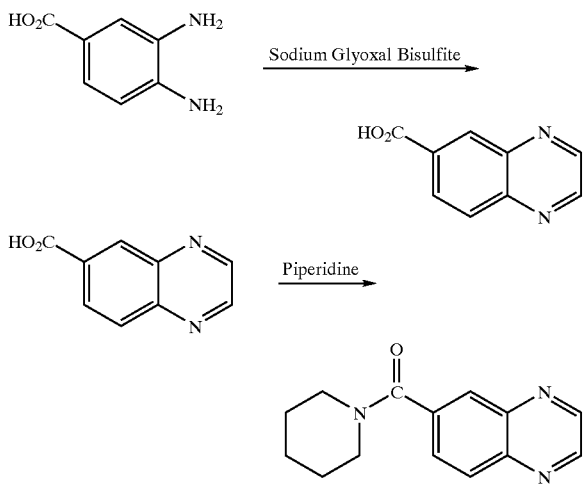

Although the preparation of AMPHAKINE CX516 appears straightforward, the synthesis requires the use of 3,4-diaminobenzoic acid, an expensive starting material. For example, preparation of the isomeric 2,3-diaminobenzoic acid employs a multi-step method that includes oxidation, reduction, amidation, nitration, separation of isomers, further reduction, and hydrolysis, as set out below (3). Preparation of the isomeric 3,4-diaminobenzoic acid can be carried out using this multi-step method by isolating and further reacting the 3-amido, 4-nitrobenzoic acid isomer.

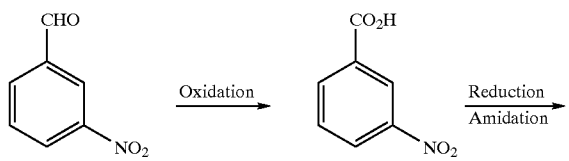

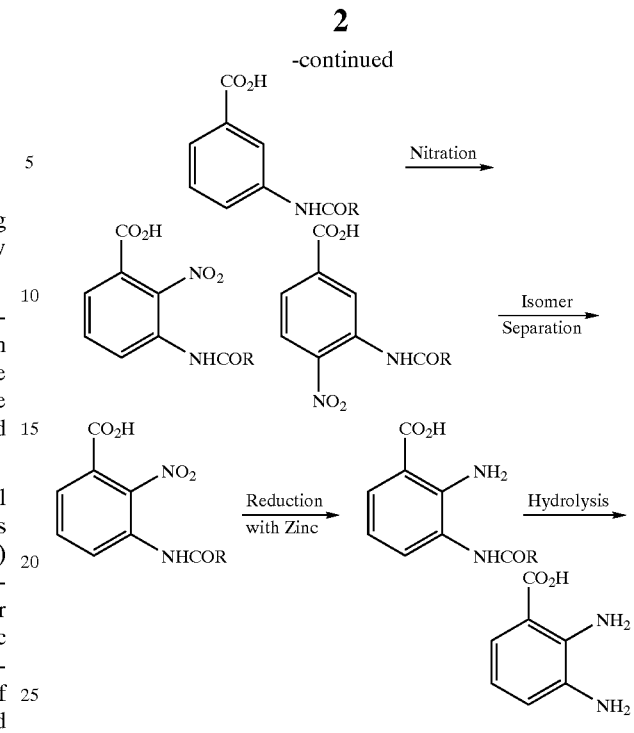

Other methods for preparing 3,4-diaminobenzoic-acid involve the electrochemical reduction of 3,4-dinitrobenzoic acid and the hydrogenation of substituted benzofurazans (4). These methods also employ expensive chemical intermediates.

Initial attempts by the applicant to prepare quinoxaline-6-carboxylic acid focused on a one step selective oxidation of the benzyl group to a carboxylic acid without affecting the aromatic rings, as set out below.

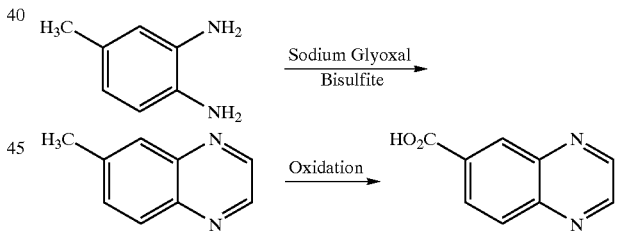

Many methods are known for the direct oxidation of benzylic methyl groups to carboxylic acids. These methods typically employ a strong oxidizing agent, such as potassium permanganate, that reacts with a methyl group providing the remainder of the molecule is not reactive to the oxidizing agent (5). Thus, toluene can be oxidized with potassium permanganate to benzoic acid without affecting the benzene ring (5). Catalytic methods are generally more acceptable for industrial scale because theses methods employ milder oxidizing agents, i.e., air or oxygen, to carry out the oxidation of benzylic methyl groups to the corresponding carboxylic acid (6). The oxidation of 5- and 6-methyl-quinoxalines to 5- and 6-quinoxaline-carboxylic acids is not so straightforward, however, because strong oxidizing agents, such as potassium permanganate, degrade the aromatic ring yielding 2,3-pyrazinedicarboxylic acid (7):

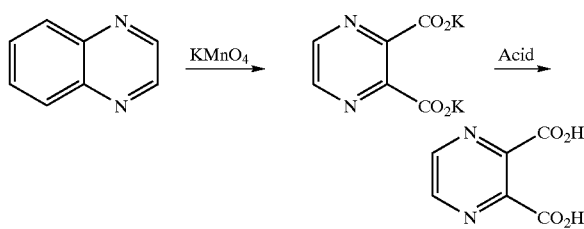

Milder oxidizing agents, i.e., air or oxygen in the presence of a catalyst, on the other hand, have no effect on the benzylic methyl group of 5- or 6-methyl-quinoxaline. Air in the presence of a cobalt salt can oxidize toluene to benzoic acid (6) but does not oxidize methyl-quinoxaline to quinoxaline-carboxylic acid. Similarly, air and oxygen in the presence of a palladium or platinum catalyst are also ineffective (8). Most known oxidizing reagents are either too mild to react with methyl-quinoxalines or are too reactive causing structural changes.

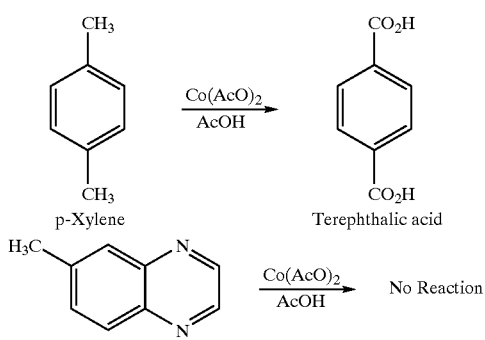

Many methods are also known for the oxidation of benzylic hydroxymethyl groups to carboxylic acids. These methods typically employ strong oxidizing agents such as those set out below.

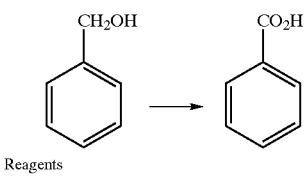

Reagents $O_2/Pt(C)$, water, reflux 10 h
Ni Anode, 1M NaOH, 25° C., 1.5 h
KOH, $H_2O$, t-BuOH, $CCl_4$, 25–80° C. 10–60 min
$ZnCr_2O_7 \cdot 3H_2O$, $CH_2Cl_2$, RT, 6 h
$NaMnO_4 \cdot H_2O$, hexane, 69° C., 6 h
$Cu(MnO_4)_2 \cdot 8H_2O$, $CH_2Cl_2$, RT, 24 h
$Bu_4NMnO_4$, Pyridine, RT
$KMnO_4$, water, Benzene, $Bu_4NBr$, RT, 3 h
$KMNO_4$, dicyclohexano-18-crown-6 ether, RT, 2 h
1.5 $NiO_2$, Benzene, 30° C., 3h
$Na_2RuO_4$, NaOH, $H_2O$, 25° C., 1 h
$K_2RuO_4$, $K_2S_2O_8$, RT, 1.5 h Thus, when choosing an oxidizing agent, it is important to consider its strength under the reaction conditions.

Because attempts to prepare quinoxaline-6-carboxylic acid via a one-step selective oxidation of the benzyl group were not successful, a multi-step method to prepare quinoxaline-6-carboxylic acid was developed. In the first step, 6-methyl-quinoxaline is halogenated to provide 6-halomethyl-quinoxaline. In the second step, 6-halomethyl-quinoxaline is converted to 6-hydroxymethyl-quinoxaline by nucleophilic displacement with a hydroxide group. In the third step, 6-hydroxymethyl-quinoxaline intermediate is selectively oxidized to quinoxaline-6-carboxylic acid.

BRIEF SUMMARY OF THE INVENTION

The present invention pertains to a method for preparing quinoxaline-5- and 6-carboxylic acids (I). The method comprises contacting an aqueous suspension of a 5-or 6-hydroxymethyl quinoxaline (II) with oxygen in the presence of a transition metal catalyst, to form the respective quinoxaline-5- or 6-carboxylic acid (I).

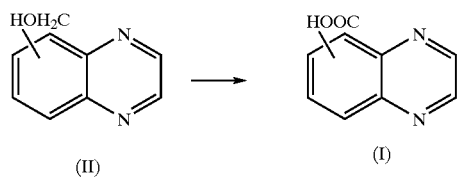

The present invention also pertains to a method for preparing a carboxylic acid selected from the group consisting of:

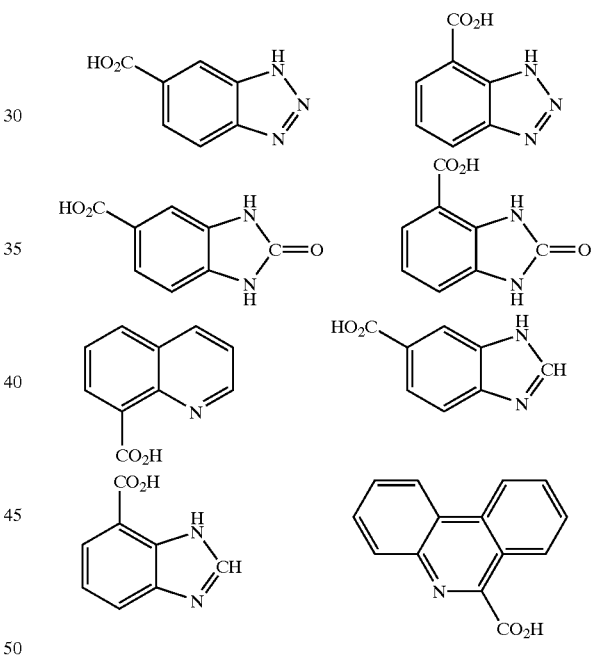

The method comprises contacting an aqueous suspension of a hydroxymethyl precursor compound of the respective carboxylic acid with oxygen in the presence of a transition metal catalyst, to form the respective carboxylic acid.

DETAILED DESCRIPTION OF THE INVENTION

The present invention pertains to a multi-step method for converting benzyl heterocyclic compounds to the corresponding carboxylic acid heterocyclic compounds. The multi-step method is especially suitable for converting 5- and 6-benzyl quinoxalines to the corresponding quinoxaline-5- and 6-carboxylic acids. The 5- and 6-benzyl quinoxalines may be prepared from ortho-diaminotoluenes, such as 2,3- and 3,4-diaminotoluene, by condensation with sodium glyoxal bisulfite. The method for oxidizing benzylic methyl groups may also be employed to prepare a wide variety of heterocyclic carboxylic acid compounds.

In the first step, 5- or 6-methyl-quinoxaline is halogenated to provide a 5- or 6-halomethyl-quinoxaline intermediate, respectively.

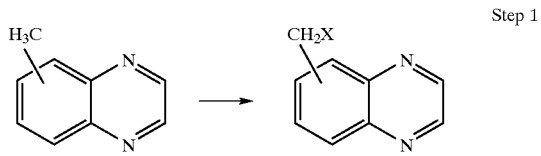

Step 1

This first step is more fully described in a patent application Ser. No. 09/909,000 entitled "Method For Preparing Halomethyl Heterocyclic Compounds" filed Jul. 19, 2001 now U.S. Pat. No. 6,492,517 by applicant and assigned to the assignee of this application, which is hereby incorporated by reference.

In the second step, the 5- or 6-halomethyl-quinoxaline intermediate is converted to 5- or 6-hydroxymethyl-quinoxaline by nucleophilic displacement with a hydroxide group, respectively.

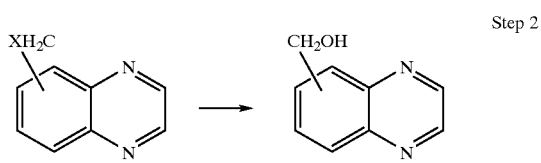

Step 2

This second step is more fully described in a patent application Ser. No. 09/909,002 entitled "Methods For Preparing 5- and 6-Benzylfunctionalized Quinoxalines" filed Jul. 19, 2001 by applicant and assigned to the assignee of this application, which is hereby incorporated by reference.

In the third step, the 5- or 6-hydroxymethyl-quinoxaline intermediate is selectively oxidized to the corresponding quinoxaline-5- or 6-carboxylic acid, respectively.

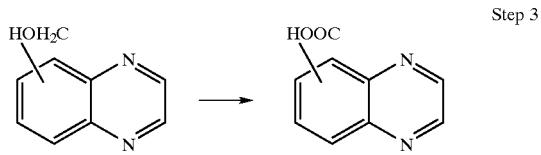

Step 3

As set out above, 5- and 6-benzyl quinoxalines may be prepared from ortho-diaminotoluenes, such as 2,3- and 3,4-diaminotoluene, by condensation with sodium glyoxal bisulfite. For example, 6-benzyl quinoxaline may be prepared by condensation of 3,4-diaminotoluene with sodium glyoxal bisulfite (9).

Because attempts to prepare quinoxaline-6-carboxylic acid via a one-step selective oxidation of the benzyl group were not successful, a multi-step method to prepare quinoxaline-6-carboxylic acid was developed. In the first step, 6-methyl-quinoxaline is halogenated to provide 6-halomethyl-quinoxaline. In the second step, 6-halomethyl-quinoxaline is converted to 6-hydroxymethyl-quinoxaline by nucleophilic displacement with a hydroxide group. In the third step, 6-hydroxymethyl-quinoxaline intermediate is selectively oxidized to quinoxaline-6-carboxylic acid.

In the first step of the synthesis, a benzylic methyl heterocyclic compound and a halogenating agent, such as N-chlorosuccinimide (NCS) or N-bromosuccinimide (NBS), are reacted in the presence of a radical initiator, such as benzoyl peroxide or azobisisobutyronitrile, in a suitable solvent, to form the respective halomethyl heterocyclic compound, such as 5- or 6-halomethyl quinoxaline.

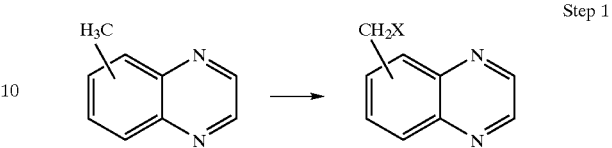

Step 1

Suitable solvents may be selected from the group consisting of fluorobenzene, difluorobenzenes, trifluorobenzenes, chlorobenzene, dichlorobenzenes, trichlorobenzenes, α, α, αxtrifluorotoluene and α, α, αtrichlorotoluene.

The method for halogenating benzylic positions may also be employed to halogenate a variety of heterocyclic compounds. The method typically affords good yields of halomethyl-quinoxalines when [6QX]/[benzoyl peroxide] ≦40 while maintaining a temperature in the range of 60° C. to 115° C. for a period of 1 to 12 hours. Yields for benzylic brominations (conversions ≧95%, selectivities ≧97%) are in general better than for benzylic chlorinations (conversions 60%, selectivities ~75–80%). The 5- or 6-halomethyl quinoxaline may be a 5-halomethyl quinoxaline or may be a 6-halomethyl quinoxaline. The halomethyl may be a chloromethyl or may be a bromomethyl.

The method comprises contacting the benzyl precursor compound of the respective halomethyl compound with a halogenating agent in the presence of a radical initiator in a solvent selected from the group consisting of fluorobenzene, difluorobenzenes, trifluorobenzenes, chlorobenzene, dichlorobenzenes, trichlorobenzenes, α, α, α-trifluorotoiuene and α, α, α-trichlorotoluene, to form the respective halomethyl compound.

The benzylic halogenation of heterocyclic compounds, such as methylquinoxalines, depends on a variety of factors including the halogenating agent, the radical initiator, the solvent, temperature, reaction time, reagent concentrations, and procedure.

The halogenating agents may be any halogenating agent which is capable of selectively halogenating the benzylic methyl group of a heterocyclic compound. The term "halogen", as used herein, refers to the elements fluorine, chlorine, bromine, and iodine. Preferred halogens are chlorine and bromine. Non-limiting illustrative halogenating agents may be selected from the group consisting of N-chlorosuccinimide, N-bromosuccinimide, $Cl_2$, $Br_2$, t-butyl hypochlorite, N-chloroglutarimide, N-bromoglytarimide, N-chloro-N-cyclohexyl-benzenesulfonimide, and N-bromophthalimide. Preferred halogenating agents are N-chlorosuccinimide and N-bromosuccinimide.

The radical initiators may be any radical initiator which is capable of catalyzing the halogenating agent to selectively halogenate the benzylic methyl group of a heterocyclic compound. The presence of an initiator is essential for the reaction to occur because radicals propagate these reactions. Non-limiting illustrative radical initiator agents may be selected from the group consisting of benzoyl peroxide, azobisisobutyronitrile (AIBN), and diacyl peroxides, dialkyl peroxydicarbonates, and tert-alkylperoxyesters, monoperoxycarbonates, di(tert-alkylperoxy)ketals, and ketone peroxides. Preferred radical initiators are benzoyl peroxide and azobisisobutyronitrile. Alternatively, radicals can be generated photochemically.

The solvents may be any solvent which is capable of promoting the halogenating agent to selectively halogenate the benzylic methyl group of a heterocyclic compound. The solvent must (a) be a media in which the halogenating agent has a low, but definite, solubility; (b) be stable to the halogenating agent allowing the halogenating agent to react preferentially at the methyl group of the heterocyclic compound to provide a halomethyl-heterocyclic compound that is stable in the solvent under the reaction conditions; and (c) be environmentally acceptable. Most conventional benzylic bromination procedures employ highly toxic solvents which are rigorously restricted on an industrial level. Suitable solvents may be selected from the group consisting of fluorobenzene, difluorobenzenes, trifluorobenzenes, chlorobenzene, dichlorobenzenes, trichlorobenzenes, α, α, α-trifluorotoluene and α, α, α-trichlorotoluene. Preferred solvents are chlorobenzene and α, α, α-trifluorotoluene.

In the second step of the synthesis, 5- or 6-halomethyl-quinoxaline is converted to 5- or 6-hydroxymethyl-quinoxaline by nucleophilic displacement with a hydroxide group.

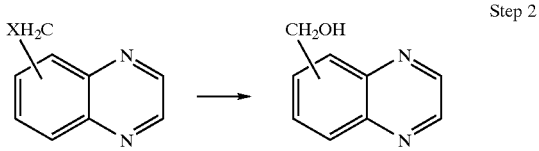

Step 2

A first embodiment for preparing a 5- or 6-hydroxymethyl-quinoxaline comprises contacting an aqueous suspension of a 5- or 6-halomethyl-quinoxaline with a water-soluble nucleophile, $N^1$, containing moiety Y.

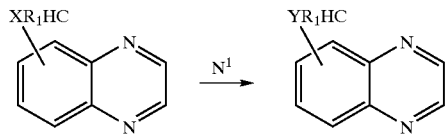

$R_1$ may be selected from the group consisting of hydrogen and branched and unbranched alkyl and aryl groups having from 1 to 9 carbon atoms. Preferably, $R_1$ is selected from the group consisting of hydrogen and branched and unbranched alkyl and aryl groups having from 1 to 6 carbon atoms, more preferably $R_1$ is selected from the group consisting of hydrogen and branched and unbranched alkyl groups having from 1 to 3 carbon atoms, and most preferably $R_1$ is hydrogen.

The water-soluble nucleophiles, $N^1$, containing moiety Y, may be any water-soluble nucleophile which is capable of selectively displacing the halogen group attached to the benzylic position of the heterocyclic compound in an aqueous suspension. The term "water-soluble nucleophile", as used herein, refers to a nucleophile that can be dissolved in water to yield a solution with a molarity equal to, or greater than, 0.01. Non-limiting illustrative water-soluble nucleophiles are those that contain a Y moiety, where Y may be selected from the group consisting of —$OR_2$, —$NHR_2$, —$NR_2R_3$, —$SR_2$, and —CN. $R_2$ and $R_3$ are independently selected from the group consisting of hydrogen and branched and unbranched alkyl groups having from 1 to 4 carbon atoms. Preferably, $R_2$ and $R_3$ are independently selected from the group consisting of hydrogen and branched and unbranched alkyl groups having from 1 to 3 carbon atoms, more preferably $R_2$ and $R_3$ are independently selected from the group consisting of hydrogen and alkyl groups having from 1 to 2 carbon atoms, and most preferably $R_2$ and $R_3$ are hydrogen. Preferred water-soluble nucleophiles may be selected from the group consisting of alkali hydroxides and alkaline earth hydroxides. More preferred water-soluble nucleophiles may be selected from the group consisting of lithium hydroxide, sodium hydroxide, and potassium hydroxide. Preferably, Y is hydroxy.

A second embodiment for preparing a 5- or 6-hydroxymethyl-quinoxaline comprises contacting a 5- or 6-halomethyl-quinoxaline with an organic solvent-soluble nucleophile, $N^2$, containing moiety Y, in an inert polar organic solvent.

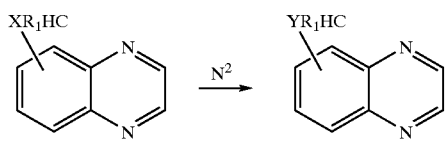

The organic solvent-soluble nucleophiles may be any organic solvent-soluble nucleophile which is capable of selectively displacing the halogen group attached to the benzylic position of the heterocyclic compound in an inert polar organic solvent. The term "organic solvent-soluble nucleophile", as used herein, refers to a nucleophile that can be dissolved in an organic solvent to yield a solution with a molarity equal to, or greater than, 0.01. Non-limiting illustrative organic solvent-soluble nucleophiles are those that contain a Y moiety, where Y may be selected from the group consisting of —$OR_2$, —$NHR_2$, —$NR_2R_3$, and —$SR_2$. $R_2$ and $R_3$ are independently selected from the group consisting of hydrogen and branched and unbranched alkyl and aryl groups having from 5 to 9 carbon atoms. Preferably, $R_2$ and $R_3$ are independently selected from the group consisting of hydrogen and branched and unbranched alkyl and aryl groups having from 5 to 8 carbon atoms, more preferably $R_2$ and $R_3$ are independently selected from the group consisting of hydrogen and branched and unbranched alkyl and aryl groups having from 5 to 7 carbon atoms, and most preferably $R_2$ and $R_3$ are hydrogen. Preferred organic solvent-soluble nucleophiles may be selected from the group consisting of benzyltrimethyl ammonium hydroxide, tetrabutyl ammonium hydroxide, alkyl alcohols, aryl alcohols, alkylamines, arylamines, alkyl sulfides, aryl sulfides, and the salts thereof. More preferred organic solvent-soluble nucleophiles are benzyltrimethyl ammonium hydroxide and tetrabutyl ammonium hydroxide. Preferably, Y is hydroxy.

The inert polar organic solvents may be any inert polar organic solvent which is capable of dissolving the organic solvent-soluble nucleophile and the 5- or 6-halomethyl quinoxaline thereby permitting the selective displacement of the halogen group attached to the benzylic position of the heterocyclic compound. The term "inert polar organic solvent", as used herein, refers to an organic solvent that does not react with the organic solvent-soluble nucleophile or the 5- or 6-halomethyl quinoxaline and promotes a reaction between the organic solvent-soluble nucleophile and the 5- or 6-halomethyl quinoxaline. Non-limiting illustrative inert polar organic solvents may be selected from the group consisting of tetrahydrofuran, dioxane, 2-methoxyethyl ether, triethylene glycol dimethyl ether, dimethylsulfoxide (DMSO), methyl-tert-butyl ether (MTBE), and diethyl ether. Preferred inert polar organic solvents may be selected from the group consisting of tetrahydrofuran, dioxane, 2-methoxyethyl ether, triethylene glycol dimethyl ether, and dimethylsulfoxide. More preferred inert polar organic solvents may be selected from the group consisting of tetrahydrofuran, dioxane, and 2-methoxyethyl ether. Most preferred inert polar organic solvents are tetrahydrofuran and dioxane.

A third embodiment for preparing a 5- or 6-hydroxymethyl-quinoxaline comprises contacting a 5- or 6-halomethyl-quinoxaline in an organic solvent with an aqueous solution of a water-soluble nucleophile, $N^1$, containing moiety Y, in the presence of a phase transfer catalyst.

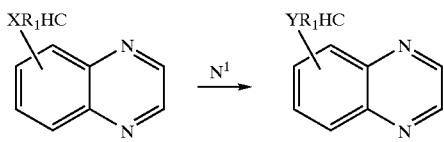

The organic solvents may be any organic solvent which is capable of dissolving the water-soluble nucleophile and the 5- or 6-halomethyl quinoxaline with the assistance of the phase transfer catalyst thereby permitting the selective displacement of the halogen group attached to the benzylic position of the heterocyclic compound. Non-limiting illustrative organic solvents may be selected from the group consisting of chlorobenzene, dichlorobenzenes, trichlorobenzenes, α,α,α-trichlorotoluene, fluorobenzene, difluorobenzenes, trifluorobenzenes, and α,α,α-trifluorotoluene. Preferred organic solvents may be selected from the group consisting of chlorobenzene, dichlorobenzenes, fluorobenzene, and difluorobenzenes. More preferred organic solvents are chlorobenzene and dichlorobenzenes. The most preferred organic solvent is chlorobenzene.

The phase transfer catalysts may be any phase transfer catalyst which is capable of dissolving the water-soluble nucleophile and the 5- or 6-halomethyl quinoxaline in the organic phase thereby permitting the selective displacement of the halogen group attached to the benzylic position of the heterocyclic compound. The phase transfer catalyst is typically an organic salt (for example, tetraalkyl-ammonium salts, benzyltrimethylammonium salts, etc) that is soluble in both the aqueous phase and the organic phase. Non-limiting illustrative phase transfer catalysts may be selected from the group consisting of tetra-n-butyl-ammonium chloride, benzyltrimethylammonium chloride, benzyltrimethylammonium hydroxide, tetralkyl ammonium salts, tetraalkyl sulfonium salts, and cetyltrimethylammonium salts.

The 5- and 6-halomethyl quinoxalines and the nucleophiles may be reacted in relative amounts ranging from about 1:1 to about 1:100, and preferably from about 1:10 to about 1:30, respectively. The 5- and 6-halomethyl quinoxalines and the nucleophiles may be reacted at temperatures ranging from about 25° C. to about 150° C., preferably from about 25° C. to about 100° C., and at pressures ranging from ambient to about 100 psig, and preferably ambient.

In the third step, the 5- or 6-hydroxymethyl-quinoxaline intermediate is selectively oxidized to the corresponding quinoxaline-5- or 6-carboxylic acid, respectively. The method comprises contacting an aqueous suspension of a 5- or 6-hydroxymethyl quinoxaline (II) with oxygen in the presence of a transition metal catalyst, to form the respective quinoxaline-5- or 6-carboxylic acid (I).

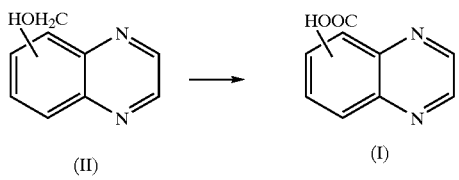

The method for oxidizing benzylic methyl groups may also be employed to prepare a wide variety of heterocyclic carboxylic acid compounds. In another preferred embodiment, the invention is directed to a method for preparing a carboxylic acid selected from the group consisting of:

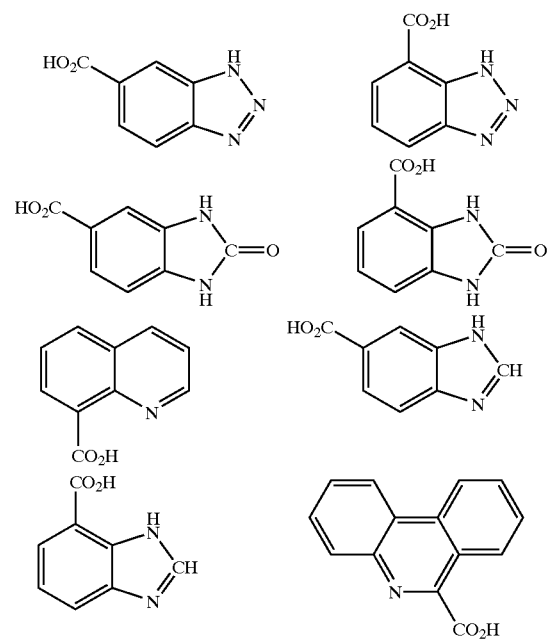

The method comprises contacting an aqueous suspension of a hydroxymethyl precursor compound of the respective carboxylic acid with oxygen in the presence of a transition metal catalyst, to form the respective carboxylic acid.

The method for oxidizing benzylic hydroxymethyl compounds, such as hydroxymethyl-quinoxalines, depends on a variety of factors including the aqueous suspension, the source of oxygen, the transition metal catalyst, temperature, reaction time, reagent concentrations, and procedure.

The aqueous suspension may be any aqueous suspension of a 5- or 6-hydroxymethyl quinoxaline (II) having a pH value which is capable of selectively oxidizing the benzylic hydroxymethyl group of a heterocyclic compound. The acid can be prepared from the alcohol in a neutral suspension, however, oxidation is more rapid in an alkaline suspension. Preferably, the aqueous suspension of a 5- or 6-hydroxymethyl quinoxaline (II) may have a pH value in the range from about 7 to about 14, preferably from about 8 to about 14, and more preferably from about 12 to about 14. Suitable sources for providing the alkalinity include alkali and alkaline earth metal oxides, hydroxides, carbonates, and tetraalkylammonium hydroxide salts.

The source of oxygen may be any source of oxygen which is capable of selectively oxidizing the benzylic hydroxymethyl group of a heterocyclic compound. Oxygen, air, and mixtures thereof may be employed.

The transition metal catalysts may be any catalyst which is capable of selectively catalyzing the oxidation of the benzylic hydroxymethyl group of a heterocyclic compound. Non-limiting illustrative transition metal catalysts may be selected from the group consisting of Pd, Pt, Ru, Co, Mn, Cu, and V, especially on supports such as carbon, alumina, silica, and titania. Preferably, the transition metal catalyst is Pd/C or Pt/C.

The temperatures for preparing quinoxaline-5- and 6-carboxylic acids are important to ensure that the benzylic group is oxidized. The temperature should be chosen so that an optimum reaction rate can be reached. Such temperatures may range from about 50° C. to about 150° C., preferably from about 80° C. to about 120° C.

The reaction times play an important role in the method for preparing quinoxaline-5- and 6-carboxylic acids. Thus, reaction times should be optimum to ensure maximum conversion. Suitable reaction times may range from about 4 to about 72 hours, preferably from about 8 to about 48 hours.

The reagent concentrations should be optimum to ensure maximum conversion. The quinoxaline concentrations may range from about 0.05M to about 0.5M, preferably from about 0.1M to about 0.3M. The alkali concentration may range from about 0.5M to about 3M, preferably from about 0.9M to about 1.5M.

The method of the present invention has been used for the synthesis of quinoxaline-6-carboxylic acid, a precursor for AMPHAKINE CX516 (I), but other carboxylic acids may also be prepared by the methods of the present invention. In particular, substrates that are fragile towards strong oxidants but are impervious towards mild oxidizing agents (i.e. quinolines, triazoles, ureas derived from ortho-diaminotoluenes, etc) can be oxidized to their corresponding acids. Examples of carboxylic acids that can be made by the present method are:

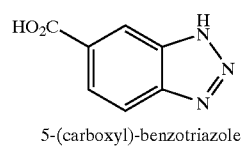
5-(carboxyl)-benzotriazole

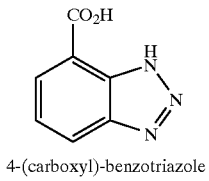
4-(carboxyl)-benzotriazole

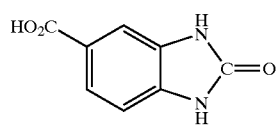
5-(carboxyl)-ureaOTD

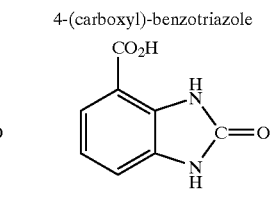
4-(carboxyl)-ureaOTD

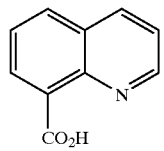
8-(carboxyl)-quinoline

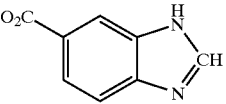
5-(carboxyl)-benzoimidazole

-continued

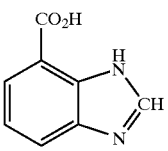
4-(carboxyl)-benzoimidazole

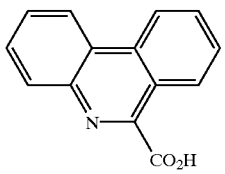
9-(carboxyl)-phenanthridine

After oxidation of the hydroxymethyl-quinoxaline, the product can remain in the aqueous solution as a salt of the quinoxaline-carboxylic acid (i.e., sodium 6-quinoxaline carboxylate). The resulting aqueous solution can then be extracted if necessary with ether (to remove any remaining organic contaminant) followed by acidification with a mineral acid. The pale yellow solid that precipitates (i.e. 6-quinoxaline carboxylic acid) can be filtered, washed with water, and air-dried (80% yield). The typical yield for the first step (halomethyl-quinoxaline synthesis) is 97% selectivity and 95% conversion. The typical yield for the second step (hydroxymethyl-quinoxaline synthesis) is 80% conversion. The typical yield for the third step (oxidation step) is 80%.

All attempts by applicant to prepare quinoxaline-6-carboxylic acid directly from 6-methyl-quinoxaline failed (i.e., without making the hydroxymethyl-quinoxaline intermediate). These attempts included air oxidation with cobalt catalyst in acetic acid; air oxidation with Co/Mn/Cl$^-$/Br$^{--}$ catalyst in acetic acid; air oxidation with 5% Pd/C catalyst; KMnO$_4$; KCrO$_4$; and ruthenium catalyst in the presence of sodium hypochlorite.

There are several advantages in using the present method compared to conventional methods. The present method is simple because the new method can convert a readily available chemical (2,3- or 3,4-diaminotoluene) into a valuable pharmaceutical intermediate in only three steps. Also, the method requires only routine operations (filtrations, distillation, extraction, etc) without the need to employ complex chemical operations or purification procedures. The present method is also economical because the method does not use exotic chemicals and it can produce the desire product in a good yield. Also, using catalytic air oxidation creates fewer environmental problems typically associated with oxidation procedures that rely on metal-oxo compounds (i.e.; potassium permanganate). Because the new method takes advantage of diaminotoluenes as a raw material, the synthesis of 6-quinoxaline-carboxylic acid is less laborious and more economical.

Throughout this disclosure, applicant may suggest various theories or mechanisms by which applicant believes the present methods function. While applicant may offer various mechanisms to explain the present invention, applicant does not wish to be bound by theory. These theories are suggested to better understand the present invention but are not intended to limit the effective scope of the claims.

The present invention is further illustrated by the following examples which are presented for purposes of demonstrating, but not limiting, the preparation of the compounds and compositions of this invention.

EXAMPLE 1

Catalytic Air Dehydrogenation of 6-Hydroxymethyl-methyl-quinoxaline With 5% Pd/C In a 500 ml flask, 6-methyl-quinoxaline (10 g, 69.4 mmol) was dissolved together with N-chlorosuccinimide (14 g, 105.3 mmol) and benzoyl peroxide (0.4 g, 1.65 mmol) in 240 g of acetonitrile. The flask was connected to a reflux-condenser and the solution was refluxed for 6 hours followed by another addition of 0.1 g of benzoyl peroxide. Reflux continued for a total reaction time of 12 hours. The solution was then analyzed showing the formation of 6-chloromethyl-quinoxaline (80% selectivity and 60% conversion according to GC analysis). The acetonitrile solution was concentrated by vacuum distillation to give a yellow suspension that was extracted with pentane (10 times, 50 ml each). The pentane extracts contained all the quinoxaline products while the residue was composed mainly of succinimide and unreacted N-chlorosuccinimide. The pentane extracts were vacuum dried to give 9.2 g of a yellow solid. GC-MS analysis showed that 80% of the extracted yellow solid was composed of 6-chloromethyl-quinoxaline (M+= 178) while the remaining 20% corresponded mainly to unreacted 6-methyl-quinoxaline. The chloro-compound was analyzed by 1H NMR showing the following resonances: 1H NMR (CDCl$_3$): 4.69 ppm (—CH$_2$Cl), 7.97 ppm (singlet, 1H), 7.68 ppm (1H, doublet, J=10 Hz), 7.98 (1H, doublet, J=10Hz), 8.73 (2H, broad doublet). These analyses confirmed the structure of the desired compound.

A sample of 6-chloromethyl-quinoxaline (1.6 g) was then mixed with an alkaline solution (1.29 g of sodium hydroxide pellets dissolved in 25 g of water) to give upon mild heating a reddish color suspension that turned into a solution. Analysis of this solution showed the presence of 6-hydroxymethyl-quinoxaline that was not isolated but rather oxidized in-situ. The catalyst was added (0.2 g of 5% Pd/C) and the solution was heated to 85–90° C. with air sparging. After eight hours reflux, the reaction was monitored by GC-MS showing the appearance of 6-quinoxaline-carboxaldehyde in the reaction mixture but all the alcohol and aldehyde were completely consumed after 48 hours. The suspension was then filtered to give a yellow/amber clear solution. The aqueous solution was cooled and extracted with ether to remove any remaining organic contaminants followed by acidification with 1M sulfuric acid. Upon acidification, a pale yellow solid precipitated which was filtered, washed with water and air dried (1.0 g, ~80% yield). The yellow powder was analyzed by infrared spectroscopy and nuclear magnetic resonance. Infrared spectroscopy showed a C=O stretching at 1708 cm$^{-1}$ which is typical for carboxylic acids, while 1H NMR (d4-MeOH) gave the following resonanes: 8.19 (d, 1H), 8.40 (dxd, 1H), 8.78 (1H), 8.99 (2H). MS analysis showed the following fragments 174 (M+), 157 (M+—OH), 129 (M+—OH—CO), 103 (M+—OH—CO—C$_2$H$_2$). The analysis are in agreement with the structure of 6-quinoxaline-carboxylic acid. The presence of the carboxylic acid group was also confirmed by ND3 proton exchange mass spectroscopy (M+=175).

EXAMPLE 2

Catalytic Air Dehydrogenation of 6-Hydroxymethyl-methyl-quinoxaline With 5% PD/C In a 100 ml flask, 6-methyl-quinoxaline (1.25 g, 8.68 mmol) was dissolved with N-bromosuccinimide (2.32, 13.0 mmol) and benzoyl peroxide (0.15 g, 0.62 ml) in 31 g of chlorobenzene. The mixture was heated to 85° C. to give a pale yellow solution that slowly turned red. The solution was maintained at 85° C. for two hours and then it was cooled to room temperature with the formation of a precipitate mainly composed of succinimide. The solution was then mixed with an equal volume (31 ml) of pentane to ease the precipitation of succinimides (NHS as well as any unreacted NBS). After filtration, the orange solid obtained (1.4 g) was extracted few times with pentane (4 times, 50 ml each) to recover any remaining 6-bromomethyl-quinoxaline. The extracts were combined with the yellow solution of bromomethyl-quinoxaline and vacuum dried to give a yellow solid (1.92 g). This solid was then reacted with 30 ml of a 1.7 M solution of sodium hydroxide to give a solution of 6-hydroxymethyl-quinoxaline that was catalytically oxidized (0.2 g 5% Pd/C) with air at 85–95° C. for 48 hours. The black suspension was filtered to give an amber solution that was neutralized with dilute sulfuric acid to give a yellow powder (1.28 g, 85% yield) that precipitated from solution (6-quinoxaline carboxylic acid).

EXAMPLE 3

Catalytic Air Dehydrogenation of 6-Hydroxymethylmethyl-quinoxaline With 5% Pt/C

In a 100 ml flask, 6-methyl-quinoxaline (1.25 g, 8.68 mmol) was dissolved with N-bromosuccinimide (2.32, 13.0 mmol) and benzoyl peroxide (0.15 g, 0.62 mml) in 31 g of chlorobenzene. The mixture was heated up to 85° C. to give a pale yellow solution that turned reddish with time. The solution was maintained at 85° C. for two hours and it was then cooled to −10° C. and filtered. The solution was vacuum dried to give an orange solid residue. The orange solid was then mixed with an alkaline solution prepared by dissolving 2.6 g of sodium hydroxide pellets in 50 ml of water. The mixture was gently heated to 85–95° C. to give a solution of 6-hydroxymethyl-quinoxaline that was mixed with the catalyst (5% Pt/C, 0.2 g) and maintained at that temperature with air sparging. The reaction was monitored by GCMS showing the consumption of 6-hydroxymethyl-quinoxaline and the formation of 6-quinoxalinecarboxaldehyde. After 10 hours, both compounds were completely consumed indicating the end of the reaction. The aqueous solution was cooled to room temperature and filtered. The yellow solution obtained was neutralized with 3.18 g of 96% sulfuric acid dissolved in 5 ml of water. A yellow precipitated was formed during the addition of acid. The yellow solid was filtered and air dried to give 0.67 g of dry product (45% yield). The lower yield in this experiment is attributed to a loss of bromomethyl-quinoxaline that was not recovered with from the succinimides precipitate by washings with pentane as explained in Examples 1 and 2.

EXAMPLE 4

Air Dehydrogenation of 6-Hydroxymethyl-quinoxaline Dissolved in Chlorobenzene to 6-Quinoxaline Carboxylic Acid With 5% Pd/C In a 50 ml flask, 6-methyl-quinoxaline (1.25 g, 8.68 mmol) was dissolved with N bromosuccinimide (2.32 g, 13.0 mmol) and benzoyl peroxide (0.15 g, 0.62 mmol) in 31 g of chlorobenzene. The solution was stirred and heated to 85° C. for 2.0 hours and the reaction mixture was analyzed by GCMS. The molar concentrations and molar ratios of the reactants are shown below:

| Solvent | [6QX] | [NBS] | [BP] | [NBS]/{6QX} | [6QX]/[BP] |
|---------|-------|-------|------|-------------|------------|
| ClPh    | 0.31  | 0.46  | 2.2 × 10-2 | 1.5   | 14         |

The results are summarized below:

| | Reaction Time = 120 min | |
|---|---|---|
| Product | % Selectivity | % Conversion |
| 1 | 97.0 | 94.0 |
| 2 | 2.1 | 2.7 |
| Unknowns | 2.9 | 2.0 |

The chlorobenzene solution was cooled to room temperature and was mixed with aqueous alkali prepared by dissolving 3.0 g of sodium hydroxide pellets in 30 ml of water. A phase transfer catalyst was added (0.1 g tetra-n-butyl ammonium chloride) to improve the solubility of the base in the organic phase. The mixture was heated to reflux to give a solution of 6-hydroxymethyl-quinoxaline as determined by GCMS. The catalyst (0.2 g 5% Pd/C) was added and the mixture was sparged with air for a few hours at 85° C. A cooled trap was placed at the exit of the reactor to trap the chlorbenzene that vaporized. After 24 hours, most of the chlorobenzene was removed by the flow of air leaving the aqueous phase inside the flask. At this point, visual inspection showed that the catalyst was not homogeneously dispersed forming black agglomerates. Monitoring the reaction showed that the catalyst was completely ineffective at this point. The poisoned catalyst was filtered from the reaction mixture followed by the addition of fresh catalyst (0.2 g). The oxidation was continued for a total reaction time of 72 hours with no further poisoning observed. The catalyst was filtered and the aqueous phase was acidified with a mineral acid (3.6 g of 96% sulfuric acid dissolved in 10 ml of water). No yellow precipitate of 6-quinoxaline-carboxylic acid was formed during the addition of acid. The precipitation was probably prevented by the presence of chloroaromatics remaining in the aqueous phase. The yellow solution was then extracted with ether (5 times, 100 ml each) to give a yellow solid (0.57 g) that presumably contained 6-quinoxaline-carboxylic acid. 1H NMR analysis showed a very complex spectrum indicating that the sample produced was not of the same quality as the one described in the previous examples. Nevertheless, the resonances corresponding to 6-quinoxaline-carboxylic acid were clearly observed. Thus, this procedure was ineffective in providing a good sample of 6-quinoxaline-carboxylic acid.

EXAMPLE 5

Dehydrogenation of 6-Hydroxymethyl-quinoxaline Prepared With Benzyltrimethyl-ammonium Hydroxide in Water/THF In a 50 ml flask, 6-methyl-quinoxaline (1.25 g, 8.68 mmol) was dissolved with N bromosuccinimide (2.32 g, 13.0 mmol) and benzoyl-peroxide (0.15 g, 0.62 mmol) in 31 g of chlorobenzene. The solution was stirred with heating at 85° C. for 2.0 hours to yield a reddish solution. The solution was cooled to room temperature and one volume of pentane was added to facilitate the precipitation of succinimides. The solid was filtered (1.6 g), washed with pentane and the extracts were combined with the chlorobenzene solution. This solution was then vacuum dried to give a yellow solid mainly composed of 6-bromomethyl-quinoxaline (1.92 g). This solid was dissolved in 38 g of THF and mixed with 4.24 g of a 40% commercial aqueous solution of benzyltrimethyl ammonium hydroxide. Samples were analyzed during the course of the reaction showing a progressive conversion of 6-bromomethyl-quinoxaline into the hydroxo-derivative. The pale yellow solution was stirred at room temperature overnight until the reaction was completed and no other by-products were detected by GCMS analysis. The alkaline solution was neutralized with dilute sulfuric acid (1M) and pH adjusted with sodium bicarbonate. The solution was vacuum dried to give a yellow residue (2.5 g) that was dissolved in methylene chloride and extracted with water to remove the organic salt. The methylene chloride solutions were dried over anhydrous $MgSO_4$ and the solution evaporated to give a pale yellow solid mostly composed of 6-hydroxymethyl-quinoxaline (1.20 g,~85% yield). The product was mixed with 30 g of water containing 3.0 g of sodium hydroxide dissolved. The mixture was mixed with 0.2 g of 5% Pt/C and the reaction was heated (85–90° C.) with air sparging for 12 hours. GCMS analysis showed that the alcohol was completely consumed and no aldehyde was remaining in the reaction mixture. The carbon suspension was filtered and acidified with a solution of sulfuric acid to give 1.20 g of a yellow solid (6-quinoxaline-carboxylic acid) 92% yield.

Throughout this application, various publications have been referenced. The disclosures in these publications are incorporated herein by reference in order to more fully describe the state of the art.

1. R. Granger, S. Deadwyler, M. Davis, B. Moskovitz, M. Kessler, G. Rogers, G. Lynch, *Synapse*, 22, pp. 332–337, 1996; and (b) G. Lynch, M. Kessler, G. Rogers, J. Ambross-Ingerson, R. Granger, R. S. Schehr, *International Clinical Psychopharmacology*, 11, pp. 13–19, 1996.

2. (a) J. Gum, *J. Org. Chem.*, 30, 3982, 1965:, (b) W. H. Huang, A. R. Lee, C. I. Lin, M . H. Yen, *Yixue Yanjiu*, 13, 247–54, 1993.

3. B. Schilling, *Ber.*, 34, pp. 902–907, 1901.

4. (a) A. Tallec, *Ann. Chim. (Paris)*, 3, 164, 1968; (b) V. Cere, D. Dal Monte, E. Sardi, *Tetrahedron*, 28, 3271, 1972.

5. M. Hudlicky *"Oxidations in Organic Chemistry"*, ACS Monograph 186, 1990.

6. R. A. Sheldon, J. K. Kochi, *"Metal-Catalyzed Oxidation of Organic Compounds"*, Chapter 5, pp. 121–151, Academic Press, 1981.

7. 2,3-Pyrazinedicarboxylic acid: *"Organic Synthesis"* Coll. Vol. 4 pp. 824–827, J. Wiley & Sons, Inc. NY, 1963.

8. R. A. Sheldon, J. K. Kochi, *"Metal-Catalyzed Oxidation of Organic Compounds"* Chapter 7, pp. 189–214, Academic Press, 1981.

9. J. C. Cavagnol, F. Y. Wiselogle, *J. Am. Chem. Soc.*, 69, 795, 1947.

10. Thomas D. Waugh, *NBS: N-Bromosuccinimide Its Reactions and Uses*; Arapahoe Chemicals, Inc. Boulder Co. 1951.

11. D. F. Gavin, U.S. Pat. No. 3,690,963 (1976).

12. Benzoyl Piperidine: *"Organic Synthesis"*, Coll. Vol. 1 pp. 108–110, J. Wiley & Sons, Inc. New York, 1943.

13. 2,3-Pyrazinedicarboxylic acid: *"Organic Synthesis"* Coll. Vol. 4 pp. 824–827, J. Wiley & Sons, Inc. NY., 1963.

While a number of embodiments of this invention have been represented, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

I claim:

1. A method for preparing quinoxaline-5- and 6-carboxylic acids (I) which comprises contacting an aqueous suspension of a 5- or 6-hydroxymethyl quinoxaline (II) with oxygen in the presence of a transition metal catalyst, to form the respective quinoxaline-5- or 6-carboxylic acid (I)

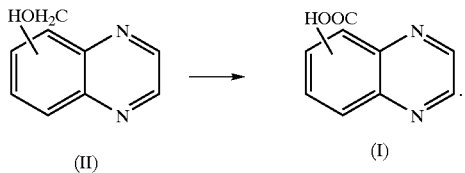

2. The method according to claim 1, wherein the quinoxaline-5- or 6-carboxylic acid is a quinoxaline-5-carboxylic acid (I).

3. The method according to claim 1, wherein the quinoxaline-5- or 6-carboxylic acid is a quinoxaline-6-carboxylic acid (I).

4. The method according to claim 1, wherein the aqueous suspension of a 5- or 6-hydroxymethyl quinoxaline (II) has a pH value in the range from about 8 to about 14.

5. The method according to claim 1, wherein the transition metal catalyst is selected from the group consisting of Pd, Pt, Ru, Co, Mn, Cu, and V.

6. The method according to claim 5, wherein the transition metal catalyst is Pd/C or Pt/C.

7. A method for preparing quinoxaline-5- or 6-carboxylic acid which comprises (1) contacting a 5- or 6-methyl quinoxaline with a halogenating agent in the presence of a radical initiator in a solvent selected from the group consisting of fluorobenzene, difluorobenzene, trifluorobenzene, chlorobenzene, dichlorobenzene, trichlorobenzene, α, α, α-trifluorotoluene and α, α, α-trichlorotoluene to form the respective 5- or 6-halomethyl quinoxaline, (2) contacting the 5- or 6-halomethyl quinoxaline with a hydroxyl-containing nucleophile to form the respective 5- or 6-hydroxymethyl quinoxaline, and (3) contacting an aqueous suspension of the 5- or 6-hydroxymethyl quinoxaline with oxygen in the presence of a transition metal catalyst, to form the respective quinoxaline-5- or 6-carboxylic acid.

* * * * *